United States Patent
Sloneker (10) Patent No.: US 12,239,038 B2
(45) Date of Patent: Mar. 4, 2025

(54) APPARATUS AND METHODS FOR MEASURING SOIL CONDITIONS

(71) Applicant: Precision Planting LLC, Tremont, IL (US)

(72) Inventor: Dillon Sloneker, Danvers, IL (US)

(73) Assignee: Precision Planting LLC, Tremont, IL (US)

( * ) Notice: Subject to any disclaimer, the term of this patent is extended or adjusted under 35 U.S.C. 154(b) by 329 days.

(21) Appl. No.: 17/998,408

(22) PCT Filed: Jun. 10, 2021

(86) PCT No.: PCT/IB2021/055112
§ 371 (c)(1),
(2) Date: Nov. 10, 2022

(87) PCT Pub. No.: WO2022/003460
PCT Pub. Date: Jan. 6, 2022

(65) Prior Publication Data
US 2023/0172092 A1      Jun. 8, 2023

Related U.S. Application Data

(60) Provisional application No. 63/047,581, filed on Jul. 2, 2020.

(51) Int. Cl.
*A01B 79/00* (2006.01)
*G01N 33/24* (2006.01)

(52) U.S. Cl.
CPC .......... *A01B 79/005* (2013.01); *G01N 33/24* (2013.01)

(58) Field of Classification Search
CPC ...... A01B 79/005; E02D 1/022; G01N 33/24; G01N 33/245
See application file for complete search history.

(56) References Cited

U.S. PATENT DOCUMENTS

| 4,554,819 A | 11/1985 | Ali |
| 4,579,003 A | 4/1986 | Riley |

(Continued)

FOREIGN PATENT DOCUMENTS

| CN | 1234471 A | 11/1999 |
| CN | 109633127 A | 4/2019 |

(Continued)

OTHER PUBLICATIONS

Kenneth A. Sudduth, Sun-Ok Chung, Pedro Andrade-Sanchez, Shrinivasa K. Upadhyaya, Field comparison of two prototype soil strength profile sensors, Computers and Electronics in Agriculture, vol. 61, Issue 1, (Year: 2008).*

(Continued)

*Primary Examiner* — Eric S. McCall
*Assistant Examiner* — Timothy P Graves (57) ABSTRACT

An apparatus for measuring a soil condition includes a shank configured to engage with a drawbar, an array of movable pads carried by the shank, and a plurality of sensors. Each of the movable pads are spaced at different distances from a point at which the shank is configured to engage the drawbar. Each sensor is coupled to at least one movable pad of the array of movable pads and configured to measure deflection of the at least one movable pad relative to the shank as the shank is dragged through soil by the drawbar. A method of measuring a property of soil includes dragging the shank through soil and measuring deflection of the movable pads relative to the shank as the shank is dragged through soil.

18 Claims, 9 Drawing Sheets

(56) References Cited

U.S. PATENT DOCUMENTS

| | | | |
|---|---|---|---|
| 4,909,335 | A | 3/1990 | Walt, Jr. |
| 5,524,560 | A | 6/1996 | Carter |
| 5,726,349 | A | 3/1998 | Palmertree et al. |
| 5,797,460 | A | 8/1998 | Wattonville et al. |
| 6,041,582 | A | 3/2000 | Tiede et al. |
| 6,062,090 | A | 5/2000 | Bachhuber et al. |
| 6,389,999 | B1 | 5/2002 | Duello |
| 6,497,153 | B1 | 12/2002 | Hoskinson et al. |
| 6,647,799 | B1 | 11/2003 | Raper et al. |
| 6,688,243 | B1 | 2/2004 | Buchholtz |
| 6,701,857 | B1 | 3/2004 | Jensen et al. |
| 6,834,550 | B2 | 12/2004 | Upadhyaya et al. |
| 6,937,939 | B1 | 8/2005 | Shibusawa et al. |
| 7,028,554 | B2 | 4/2006 | Adamchuk et al. |
| 10,178,823 | B2 | 1/2019 | Kovach et al. |
| 2003/0009286 | A1 | 1/2003 | Shibusawa et al. |
| 2003/0016029 | A1 | 1/2003 | Schuler et al. |
| 2003/0066357 | A1* | 4/2003 | Upadhyaya .............. G01N 3/58 73/818 |
| 2004/0149187 | A1 | 8/2004 | Buchholtz |
| 2005/0005704 | A1 | 1/2005 | Adamchuk et al. |
| 2005/0199045 | A1 | 9/2005 | Briaud et al. |
| 2007/0272134 | A1 | 11/2007 | Baker et al. |
| 2008/0267719 | A1 | 10/2008 | Corcoran |
| 2010/0180695 | A1 | 7/2010 | Sauder et al. |
| 2011/0073333 | A1 | 3/2011 | Rozendaal et al. |
| 2013/0180742 | A1 | 7/2013 | Wendte et al. |
| 2014/0204083 | A1 | 7/2014 | Thomson |
| 2016/0330899 | A1 | 11/2016 | Skjeveland et al. |
| 2017/0223887 | A1 | 8/2017 | Scherf et al. |
| 2018/0116092 | A1 | 5/2018 | Seifried et al. |
| 2018/0153087 | A1 | 6/2018 | Kovach |
| 2018/0168094 | A1 | 6/2018 | Koch et al. |
| 2018/0184581 | A1 | 7/2018 | Morgan et al. |
| 2018/0232674 | A1 | 8/2018 | Bilde |
| 2023/0172092 | A1 | 6/2023 | Sloneker |

FOREIGN PATENT DOCUMENTS

| | | | |
|---|---|---|---|
| EP | 3135086 | A1 | 3/2017 |
| ES | 2339315 | A1 | 5/2010 |
| GB | 2500198 | A | 9/2013 |
| SU | 1264065 | A1 | 10/1986 |
| SU | 1474546 | A1 | 4/1989 |
| WO | 03/023396 | A2 | 3/2003 |
| WO | 2020/113284 | A1 | 6/2020 |

OTHER PUBLICATIONS

Hemmat, Abbas, Tayebeh Rahnama, and Zahra Vahabi. "A horizontal multiple-tip penetrometer for on-the-go soil mechanical resistance and acoustic failure mode detection." Soil and Tillage Research 138 (2014): 17-25. (Year: 2013).*

European Patent Office, International Search Report related to International Patent Application No. PCT/IB2021/055112, mail date Aug. 23, 2021, 13 pages.

Sudduth et al., "Field comparison of two prototype soil strength profile sensors", Computers and Electronics in Agriculture v. 61, Feb. 8, 2008, p. 20-31.

Admachuk et al., "Comparison of Two Alternative Methods to Map Soil Mechanical Resistance On-the-Go", pp. 3, 2006 downloaded from chrome-extension://efaidnbmnnnibpcajpcglclefindmkaj/https://adamchukpa.mcgill.ca/presentations/ASABE_2006.pdf (Year: 2006).

Hemmat et al., "Sensor systems for measuring soil compaction: Review and analysis", pp. 89-103, 2008, downloaded from https://www.sciencedirect.com/science/ardcle/piliS0168169908001014 (Year: 2008).

Hemmat et al., "A horizontal multiple-tip penetrometer for on-the-go soil mechanical resistance and acoustic failure mode detection", 2013. pages 17-25, downloaded from https://wwwsciencedirectcom/science/articWpidS0167198713002274 (Year: 2013).

Cviklovic et al., "Data Acquisition System for On-the-Go Soil Resistance Force Sensor Using Soil Cutting Blades", 2022, pp. 1-19 downloaded from https://www.mdpi.com/1424-8220/22/14/5301 (Year: 2022).

Machado, T. M. & Lancas, K. P., Engenharia Agricola, Prototype for Soil Mechanical Resistance Measurement With Chisel Plow Automated Control, Journal of the Brazilian Association of Agricultural Engineering, vol. 36, No. 4, p. 646-655, Jul./Aug. 2016 found @ https://www.scielo.br/j/eagri/a/Z9LSWNtmrmRTGf7sZsNRCbJ/?lang=en&format=pdf.

Lui W. et al: "Development of a Texture/Soil Compaction Sensor", Proceedings International Conference On Precision Agriculture, XX, XX, Jun. 23, 1996, pp. 617-630, XP001133771.

Juan Aguera et al: "Design of a Soil Cutting Resistance Sensor for Application in Site-Specific Tillage", Sensors, vol. 13, No. 5, May 10, 2013 (May 10, 2013), pp. 5945-5957, XP055626009, DOI: 10.3390/s130505945.

Fatemeh Rahimi-Ajdadi: "A Review On the Soil Compaction Measurement Systems", 1st International and 5th National Conference on Organic vs. Conventional Agriculture, Aug. 16, 2017, pp. 1-5, XP055687349, found @: URL:https://www.researchgate.net/publication/323218205_A_REVIEW_ON_THE_SOIL_COMPACTION_MEASUREMENT_SYSTEMS.

* cited by examiner

APPARATUS AND METHODS FOR MEASURING SOIL CONDITIONS

CROSS-REFERENCE TO RELATED APPLICATION

This application is a national phase entry under 35 U.S.C. § 371 of International Patent Application PCT/IB2021/055112, filed Jun. 10, 2021, designating the United States of America and published in English as International Patent Publication WO 2022/03460 A1 on Jan. 6, 2022, which claims the benefit of the filing date of U.S. Provisional Patent Application 63/047,581, "APPARATUS AND METHODS FOR MEASURING SOIL CONDITIONS," filed Jul. 2, 2020, the entire disclosure of which is incorporated herein by reference.

FIELD

Embodiments of the present disclosure relate to measurement of soil conditions. More particularly, embodiments of the present invention relate to apparatus and methods for measuring soil compaction.

BACKGROUND

Crop yields are affected by a variety of factors, such as seed placement, soil quality, weather, irrigation, and nutrient applications. Soil compaction affects how seeds are placed, as well as how water and fertilizer permeates the soil. Thus, tests have been developed to measure soil compaction in agricultural fields. As used herein, the term "soil compaction" is a measure of the volume of solid material within a given volume of soil as compared to the volume of liquid or gases (e.g., in pores between particles of solid material). Soil compaction is proportional to soil density of dry soil. Information about soil compaction is valuable because it assists farmers with determining how deep to plant seeds, how much water and fertilizer to apply, etc. Furthermore, soil compaction is related to the force required to break through soil so that seeds can be planted below the surface. Crop yield can also be affected by soil compaction. Significant changes in soil compaction or soil density in the soil profile of the root zone of a plant can adversely affect crop yield. For example, a large change in soil compaction may cause roots to change direction when they reach the soil with high compaction. Soil compaction typically varies throughout a field and with depth beneath the surface. A no-till field could have a higher soil density or soil compaction compared to tilled field, all other variables being equal, but the density and compaction of the no-till field could still be within acceptable ranges. Therefore, the no-till field may still produce similar or better crop yield than the tilled field if rapid and significant soil density changes are minimized. Information about the density and compaction can help farmers make decisions about whether tilling is required or if tillage depth should increase or decrease.

Methods of measuring soil compaction are described in U.S. Pat. No. 6,834,550, "Soil Profile Force Measurement Using an Instrumented Tine," issued Dec. 28, 2004.

BRIEF SUMMARY

In some embodiments, an apparatus for measuring a soil condition includes a shank configured to engage with a drawbar, an array of movable pads carried by the shank, and a plurality of sensors. Each of the movable pads are spaced at different distances from a point at which the shank is configured to engage the drawbar. Each sensor is coupled to at least one movable pad of the array of movable pads and configured to measure deflection of the at least one movable pad relative to the shank as the shank is dragged through soil by the drawbar.

A method of measuring a property of soil includes dragging a shank through soil. A lateral surface of the shank carries an array of movable pads, and each of the movable pads are spaced at different distances from a drawbar engaging the shank. Deflection of the movable pads is measured relative to the shank as the shank is dragged through soil using a plurality of sensors coupled to the movable pads.

BRIEF DESCRIPTION OF THE DRAWINGS

While the specification concludes with claims particularly pointing out and distinctly claiming what are regarded as embodiments of the present disclosure, various features and advantages of embodiments of the disclosure may be more readily ascertained from the following description of example embodiments when read in conjunction with the accompanying drawings, in which:

DETAILED DESCRIPTION

The illustrations presented herein are not actual views of any machine, sensor, or portion thereof, but are merely idealized representations that are employed to describe example embodiments of the present disclosure. Additionally, elements common between figures may retain the same numerical designation.

The following description provides specific details of embodiments of the present disclosure in order to provide a thorough description thereof. However, a person of ordinary skill in the art will understand that the embodiments of the disclosure may be practiced without employing many such specific details. Indeed, the embodiments of the disclosure may be practiced in conjunction with conventional techniques employed in the industry. In addition, the description provided below does not include all elements to form a complete structure or assembly. Only those process acts and structures necessary to understand the embodiments of the disclosure are described in detail below. Additional conventional acts and structures may be used. The drawings accompanying the application are for illustrative purposes only, and are thus not drawn to scale.

As used herein, the terms "comprising," "including," "containing," "characterized by," and grammatical equivalents thereof are inclusive or open-ended terms that do not exclude additional, unrecited elements or method steps, but also include the more restrictive terms "consisting of" and "consisting essentially of" and grammatical equivalents thereof.

As used herein, the term "may" with respect to a material, structure, feature, or method act indicates that such is contemplated for use in implementation of an embodiment of the disclosure, and such term is used in preference to the more restrictive term "is" so as to avoid any implication that other, compatible materials, structures, features, and methods usable in combination therewith should or must be excluded.

As used herein, the term "configured" refers to a size, shape, material composition, and arrangement of one or more of at least one structure and at least one apparatus facilitating operation of one or more of the structure and the apparatus in a predetermined way.

As used herein, the singular forms following "a," "an," and "the" are intended to include the plural forms as well, unless the context clearly indicates otherwise.

As used herein, the term "and/or" includes any and all combinations of one or more of the associated listed items.

As used herein, spatially relative terms, such as "beneath," "below," "lower," "bottom," "above," "upper," "top," "front," "rear," "left," "right," and the like, may be used for ease of description to describe one element's or feature's relationship to another element(s) or feature(s) as illustrated in the figures. Unless otherwise specified, the spatially relative terms are intended to encompass different orientations of the materials in addition to the orientation depicted in the figures.

As used herein, the term "substantially" in reference to a given parameter, property, or condition means and includes to a degree that one of ordinary skill in the art would understand that the given parameter, property, or condition is met with a degree of variance, such as within acceptable manufacturing tolerances. By way of example, depending on the particular parameter, property, or condition that is substantially met, the parameter, property, or condition may be at least 90.0% met, at least 95.0% met, at least 99.0% met, or even at least 99.9% met.

As used herein, the term "about" used in reference to a given parameter is inclusive of the stated value and has the meaning dictated by the context (e.g., it includes the degree of error associated with measurement of the given parameter).

Figure 1:
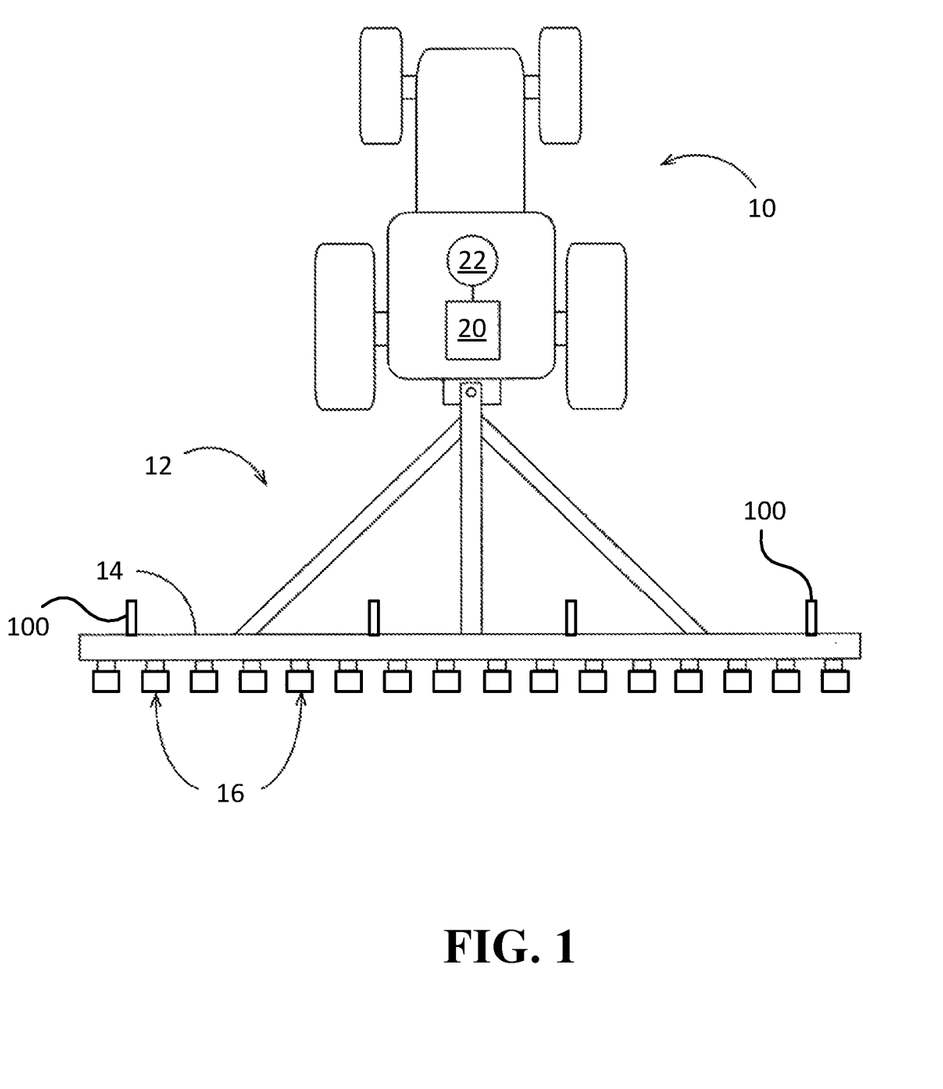
FIG. 1 is a simplified top view of a tractor drawing an agricultural implement, and including an apparatus for measuring a soil condition.

FIG. 1 is a simplified top view illustrating a tractor 10 drawing an agricultural implement 12, e.g., a tillage implement, comprising a drawbar 14 supporting tilling assemblies 16 or other tools. An implement monitor 20, which may include a central processing unit ("CPU"), memory, and graphical user interface ("GUI") (e.g., a touch-screen interface), is typically located in the cab of the tractor 10, but may be located elsewhere. A global positioning system ("GPS") receiver 22 may be mounted to the tractor 10 and connected to communicate with the monitor 20.

The tractor 10 or the implement 12 may carry one or more apparatus 100 for measuring soil conditions. For example, the apparatus 100 may be coupled to the drawbar 14. In some embodiments, the apparatus 100 may be coupled directly to a hitch of the tractor 10, or to another part of the implement 12. In FIG. 1, the implement 12 is shown carrying four of the apparatus 100, but may carry any number of the apparatus 100 (e.g., one, two, three, etc.).

Figure 2:
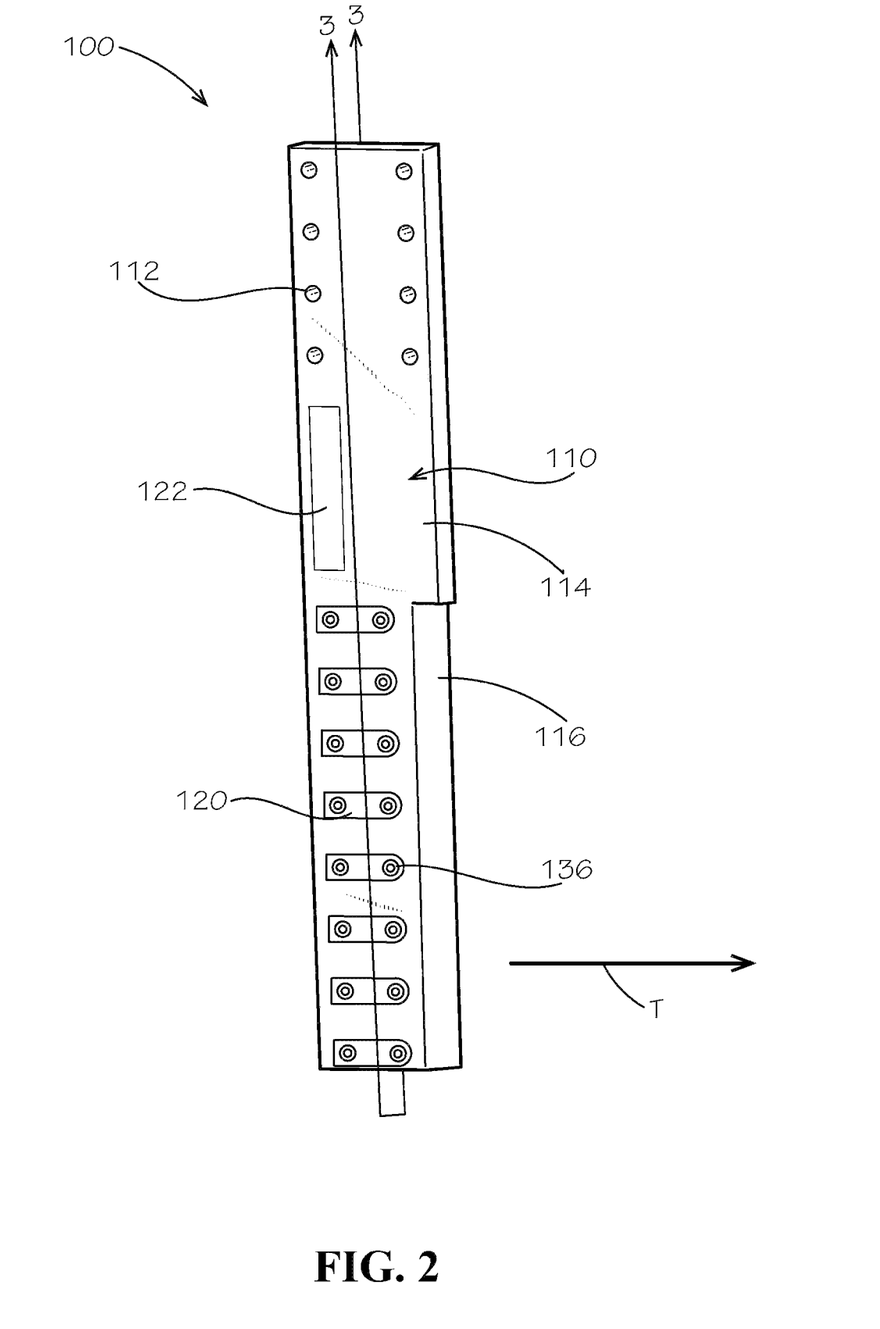
FIG. 2 is a simplified perspective view of the apparatus for measuring a soil condition.

FIG. 2 is a simplified perspective view of the apparatus 100, which includes a shank 110 configured to engage with the drawbar 14 (FIG. 1). For example, the shank 110 may include mounting holes 112 for bolts or other fasteners to connect to the drawbar 14. The mounting holes 112 may optionally be used to connect to any other selected tool, or to another mount point. For example, the shank 110 may be mounted to a set of parallel arms and a gauge wheel to set the depth of the shank 110 in the soil. The shank 110 may have generally parallel lateral surfaces 114 and tapered leading surfaces 116 (only one of each surface 114, 116 is depicted in FIG. 1). In use, the shank 110 may typically travel through the soil in a travel direction T parallel to the lateral surfaces 114.

The shank 110 may carry an array of movable pads 120 on one or both lateral surfaces 114. Each of the movable pads 120 may be spaced along the shank 110 at different distances from the end of the shank 110 or from the engagement point of the shank 110 with the drawbar. If the shank 110 has movable pads 120 on both lateral surfaces 114, the movable pads 120 on one side may be offset from the movable pads 120 on the opposite side of the shank 110 so that each movable pad 120 is a different distance from the end of the shank 110, which distances correspond to different depths in the soil. The shank 110 may also carry a strain gauge 122 or load cell configured to measure a total draft force acting on the shank 110. Though depicted on one lateral surface 114, the strain gauge 122 may be located anywhere on the apparatus 100.

Figure 3:
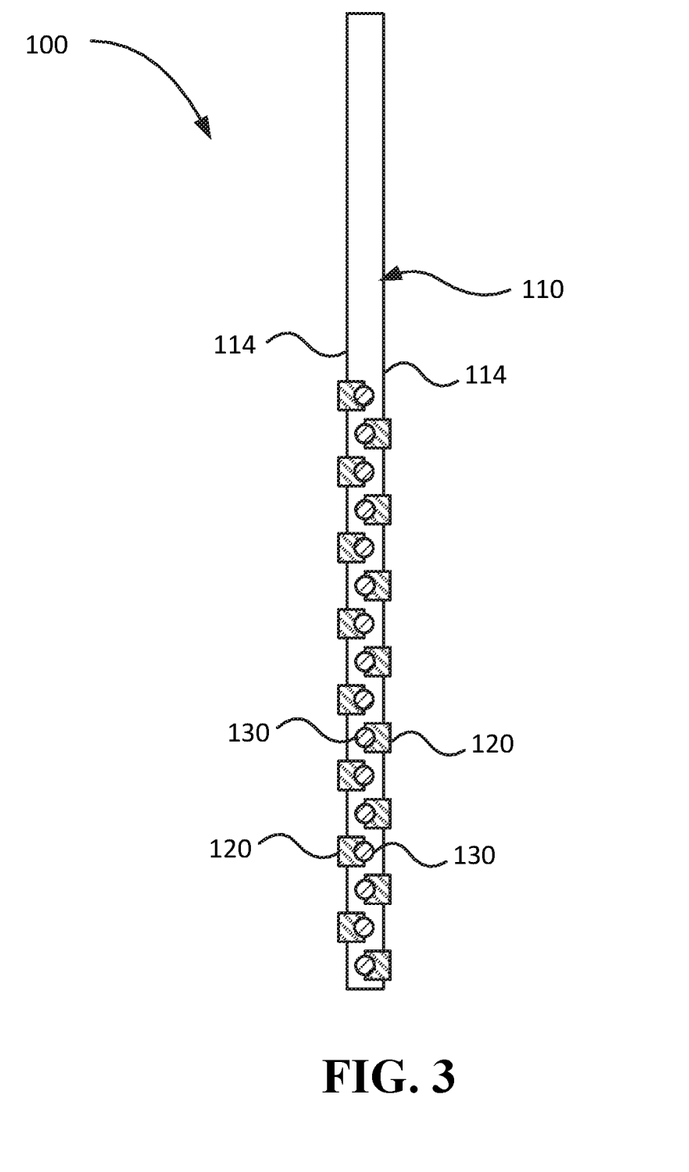
FIG. 3 is a simplified cross-sectional view of the apparatus shown in FIG. 2.

FIG. 3 is a simplified cross-sectional view of the shank 110 along line 3-3 of FIG. 2, and which shows movable pads 120 spaced on both sides of the shank 110. For example, if the movable pads 120 are spaced one inch (2.54 cm) apart from one another on each lateral surface 114 of the shank 110, the vertical distance between adjacent movable pads 120 on opposite lateral surfaces 114 may be one-half inch (1.27 cm). The movable pads 120 may be formed of a hard, wear-resistant material, such as a polymer, a metal, a composite, etc.

The shank 110 may also carry a plurality of sensors 130, each coupled to one of the movable pads 120, and configured to detect the deflection of the movable pads 120. Typically, the sensors 130 may be located behind the movable pads 120, such that the movable pads 120 protect the sensors 130 from contact with dirt and debris. Each sensor 130 may be configured to generate a signal corresponding to the deflection of a respective movable pad 120. The sensors 130 may be load cells, strain gauges, pressure sensors, or any other selected sensors.

Figure 4:
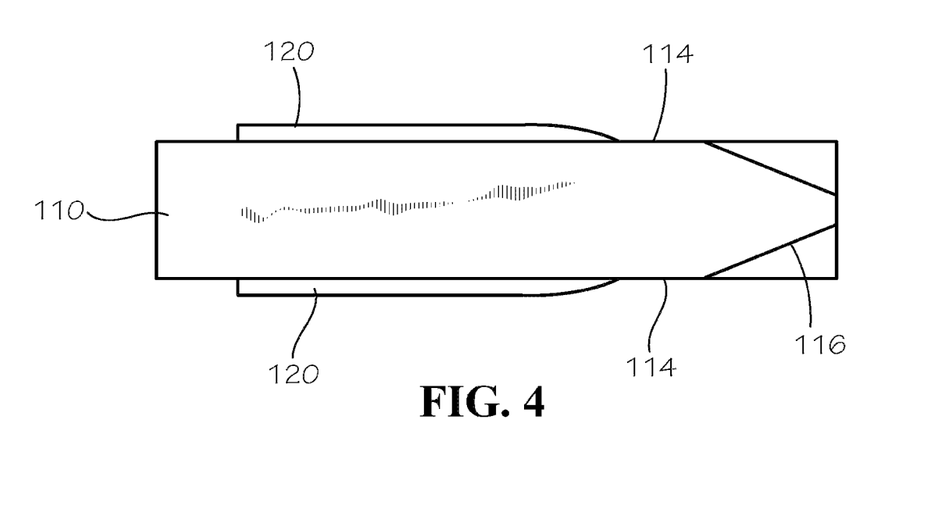
FIG. 4 is a simplified bottom view of the apparatus shown in FIG. 2.
Figure 5:
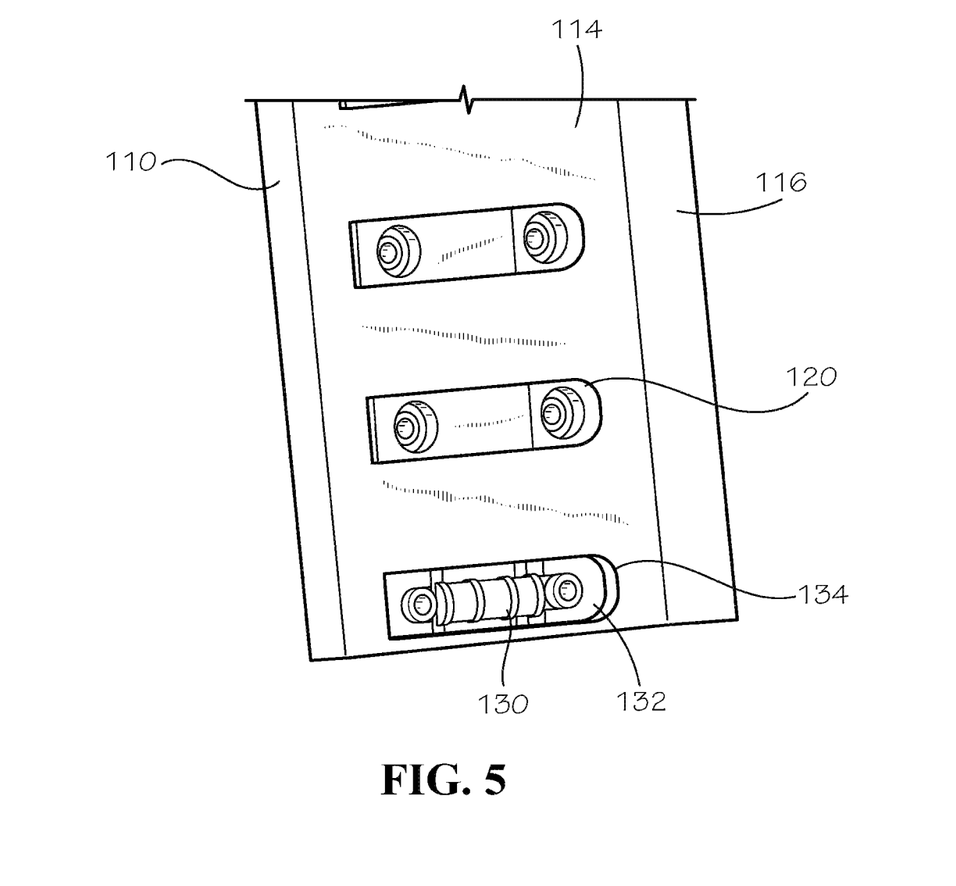
FIG. 5 is a simplified view of a portion the apparatus shown in FIG. 2, with some parts removed.

FIG. 4 is a simplified bottom view of the shank 110, and depicts the movable pads 120 extending outward past the lateral surfaces 114 thereof. The movable pads 120 may have curved or tapered front surfaces to enable the shank 110 to travel through the soil without binding the movable pads 120 on the soil. FIG. 5 is a simplified perspective view of a portion of the shank 110 with one of the movable pads 120 removed. As shown, elastic pads 132 may be disposed within pockets 134 in the shank 110. The elastic pads 132 may enable the movable pads 120 and the sensors 130 to move within the pockets 134. The elastic pads 132 may optionally transfer loads from the soil to the sensors 130. In other embodiments, the elastic pads 132 may simply allow movement of the movable pads 120, and another mechanism may transfer loads to the elastic pads 132. The movable pads 120 may be retained in the pockets 134 by flange bolts 136 (FIG. 1) or other fasteners.

Figure 6:
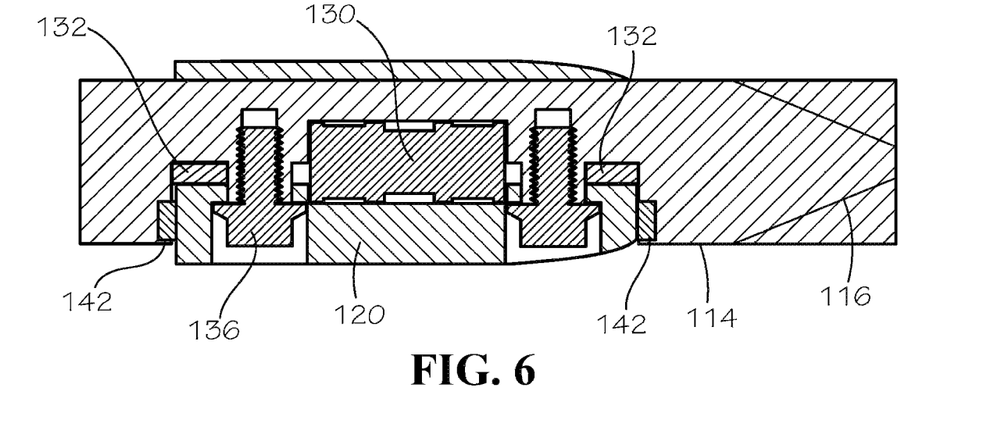
FIG. 6 is a simplified cross-sectional view showing how movable pads may be connected to the apparatus shown in FIG. 2.

FIG. 6 is a simplified side cross section of the shank 110 showing one movable pad 120, one sensor 130, and two elastic pads 132 within a pocket 134 of the shank 110. The movable pads 120 may be slidingly coupled to the shank 110 with the flange bolts 136 to enable the movable pads 120 to move inward and outward relative to the lateral surface 114. Seals 142 may be disposed between the movable pads 120 and the shank 110 to keep dirt and debris out of the space between the movable pads 120 and the shank 110. For example, the seals 142 may include an O-ring, a gasket, or another seal. The seals 142 may be formed of an elastomeric material (e.g., natural or synthetic rubber), a hard polymer, etc. The movable pad 120 may directly contact the sensor 130, such that a force applied by the soil to the movable pad 120 may be transferred to the sensor 130. The elastic pads 132 may urge the movable pad 120 outward when the force of the soil decreases (e.g., when the shank 110 is removed from the soil, or when softer soil is encountered).

Figure 7:
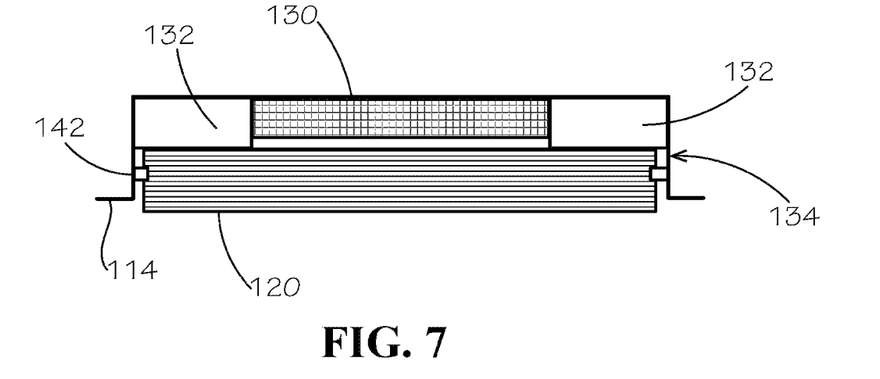
FIG. 7 is a simplified cross-sectional view showing another way movable pads may be connected to the apparatus shown in FIG. 2.

FIG. 7 is a simplified side cross section of a portion of the shank 110 illustrating another way the movable pad 120 may be coupled to the sensor 130. In particular, the movable pad 120 may press directly on the elastic pads 132. This force deforms the elastic pads 132, which therefore apply a force on the sensor 130. That is, the movable pad 120 may apply a compressive strain to the elastic pads 132, and the elastic pads 132 exert a stress in response, which stress pushes on the sensor 130.

Figure 8:
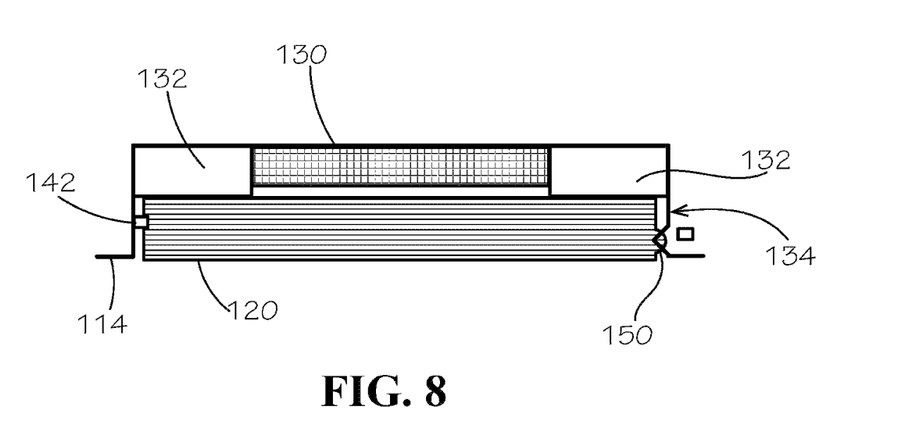
FIG. 8 is a simplified cross-sectional view showing another way movable pads may be connected to the apparatus shown in FIG. 2.

FIG. 8 is a simplified side cross section illustrating another way the movable pad 120 may be coupled to the sensor 130. The movable pad 120 may pivot about a hinged joint 150, and one end of the movable pad 120 may press on an elastic pad 132 (as shown in FIG. 8) or directly on the sensor 130 (e.g., as shown in FIG. 6).

Figure 9:
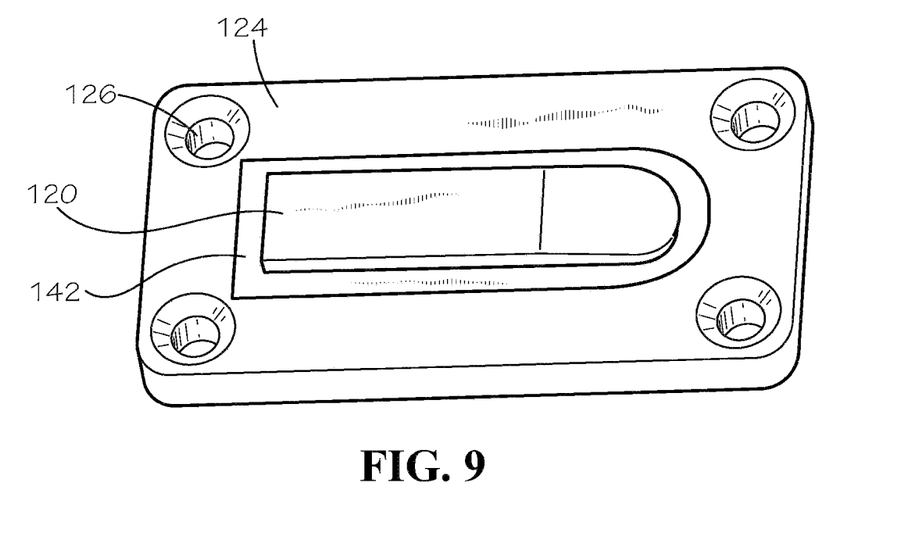
FIG. 9 is a simplified perspective view of another embodiment of movable pads that may be connected to the apparatus shown in FIG. 2 by a base plate.

FIG. 9 illustrates an embodiment in which a movable pad 120 is coupled to a base plate 124 by a seal 142. The base plate 124 may have mounting holes 126 to enable each base plate 124 to be individually secured to the shank 110 (and thus, individually replaced, in the event one movable pad 120 becomes damaged).

Figure 10:
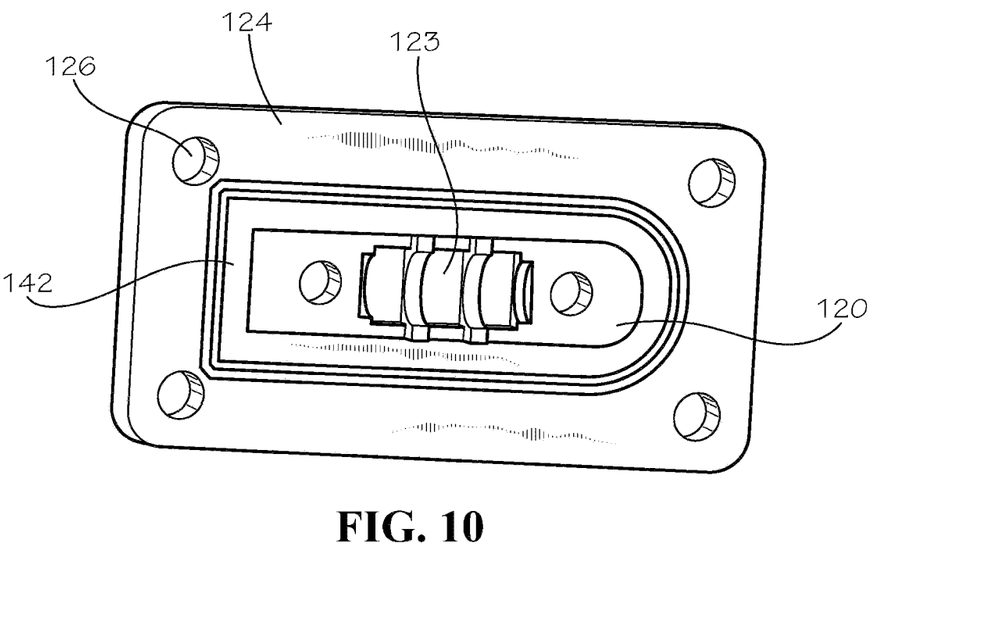
FIG. 10 illustrates a view of the opposite side of the base plate and movable pad shown in FIG. 9.

FIG. 10 illustrates a view of the opposite side of the base plate 124 and the movable pad 120. The seal 142 may be bonded to the movable pad 120 and/or the base plate 124 to provide structure and a fluid-tight seal. The seal 142 may flex enough to enable the movable pad 120 to move freely inward and outward, yet may still prevent soil from entering between the base plate 124 and the movable pad 120. The movable pad 120 may a void 123 shaped to receive the sensor 130 (see, e.g., FIG. 5). The movable pad 120 may also define one or more holes 125 shaped to receive alignment pins protruding from the shank 110, which may enable the movable pad 120 to move inward toward and outward from the shank 110, while preventing fore-and-aft, vertical, and twisting movement. Thus, the holes 125 and alignment pins may help isolate movement other than movement inward and outward.

The implement monitor 20 of the tractor 10 (FIG. 1) may include a receiver (e.g., wired or wireless) configured to receive signals from the sensors 130. The implement monitor 20 may calculate a property of the soil, such as soil hardness. The implement monitor 20 may also include a transmitter configured to transmit the property of the soil, such as to a controller, another vehicle, a network (e.g., the internet), etc.

Figure 11:
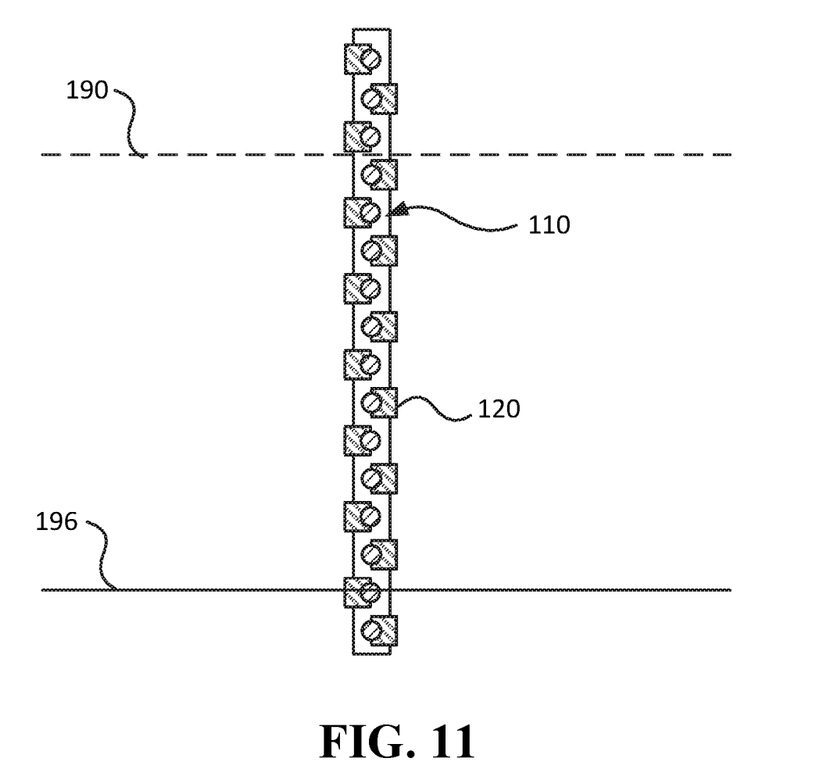
FIG. 11 is a simplified cross-sectional view of the apparatus of FIG. 2 traveling through soil.
Figure 12:
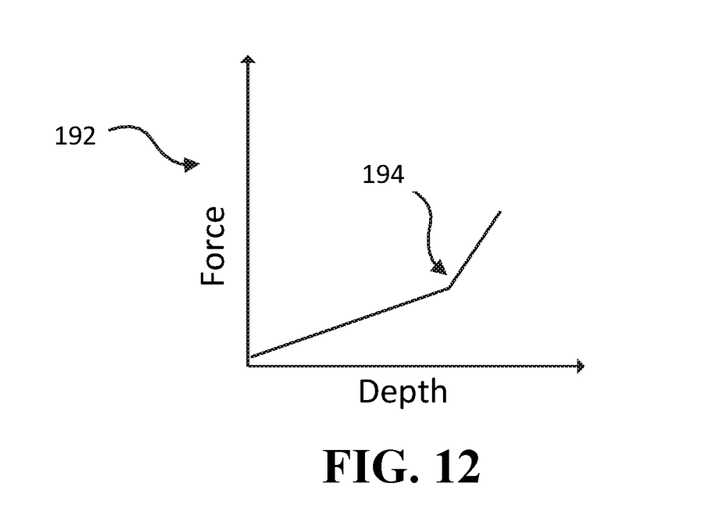
FIG. 12 is graph showing force applied to movable pads as a function of depth in soil.

FIG. 11 is a simplified cross-sectional view of the shank 110 traveling through soil. A portion of the shank 110 is below a surface 190 of the soil, including at least some of the movable pads 120. The sensors 130 (FIG. 5) measure deflection of the movable pads 120 and calculate forces on the movable pads 120. Because the movable pads 120 are arranged in an array with known locations, the implement monitor 20 (FIG. 1) may correlate the force on the movable pads 120 to a depth in the soil, visualized in the graph 192 shown in FIG. 12. The soil density generally increases with depth, and a point 194 at which the slope of the graph 192 changes may identify a depth of a compaction layer 196 or hard pan. Identification of the compaction layer 196 may enable a farmer to change tillage, seeding, fertilizing, watering, or other parameters, at the time of the measurement or at any later time. For example, the implement monitor 20 may generate a map of a field with depth of the compaction layer 196, which may be used to identify portions of the field for additional tilling, different seed populations, different seed depths, etc.

Figure 13:
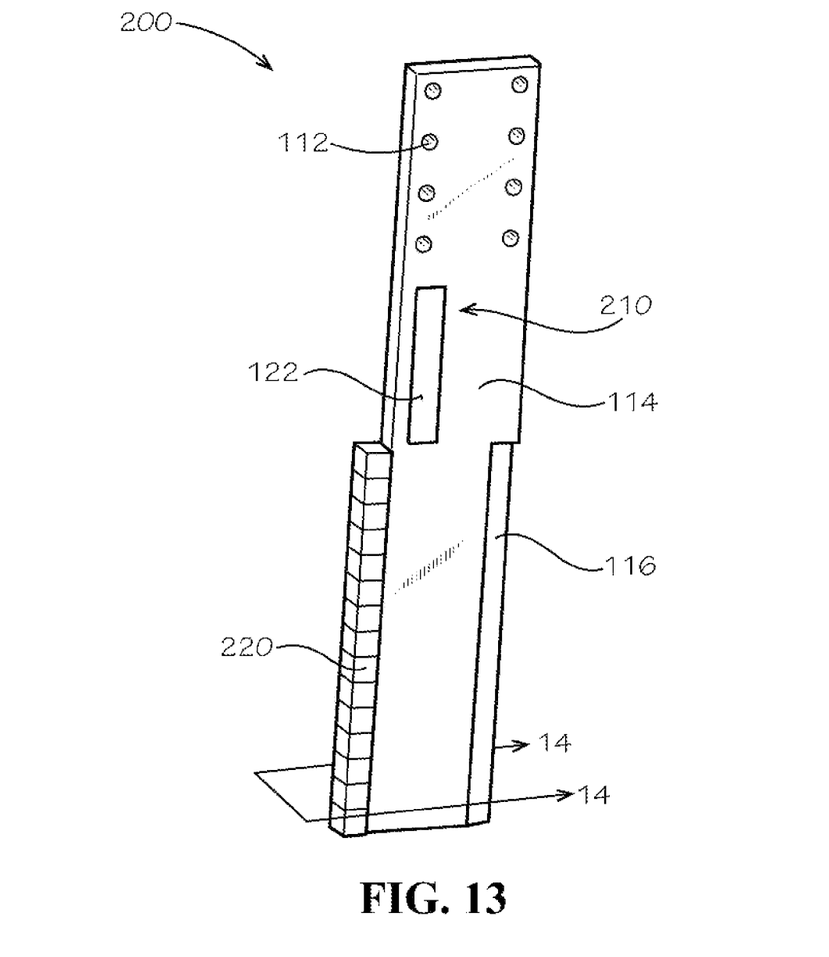
FIG. 13 is a simplified perspective view of another apparatus for measuring a soil condition.

FIG. 13 is a simplified perspective view of another apparatus 200, which includes a shank 210 configured to engage with the drawbar 14 (FIG. 1) via mounting holes 112. The mounting holes 112 may optionally be used to connect to any other selected tool, or to another mount point. The shank 110 may have generally parallel lateral surfaces 114 and tapered leading surfaces 116 (only one of each surface 114, 116 is depicted in FIG. 1).

The shank 210 may carry an array of movable pads 220 along the rear of the shank 210, rearward of the lateral surfaces 114. The shank 210 may also carry a strain gauge 122 or load cell configured to measure a total draft force acting on the shank 210.

Figure 14:
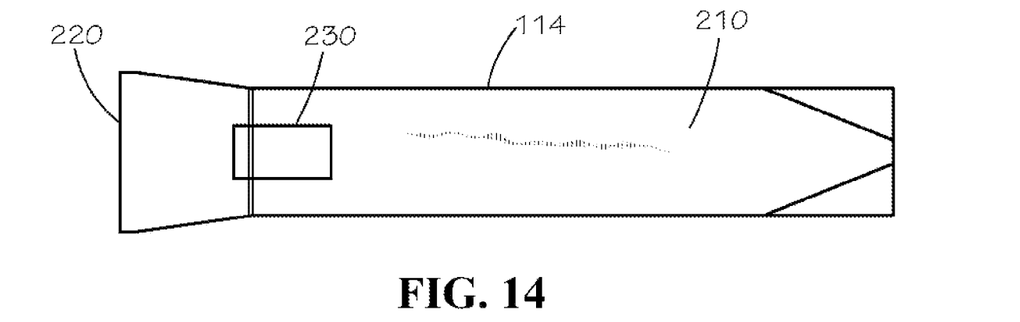
FIG. 14 is a simplified cross-sectional view of the shank of the apparatus shown in FIG. 13.

FIG. 14 is a simplified cross-sectional view of the shank 210 along line 14-14 of FIG. 13, and which shows that the movable pad 220 along the rear of the shank 210 may be flared outward past the lateral surfaces 114, such as in a generally trapezoidal shape. The movable pads 220 in this embodiment may measure draft forces (i.e., the force required to drag the movable pads 220 through the soil), rather than compressive forces, which may be measured by the apparatus 100 shown in FIG. 2. As soil density increases, draft force also increases. The angle and length of the surfaces of the movable pads 220 may affect the draft force applied to the movable pads 220. The movable pads 220 may be connected to the shank 110 by a load cell 230, which is in tension when the shank 110 is dragged through soil.

The shank 110 may also carry a plurality of sensors 130, each coupled to one of the movable pads 120, and configured to detect the deflection of the movable pads 120. Typically, the sensors 130 may be located behind the movable pads 120, such that the movable pads 120 protect the sensors 130 from contact with dirt and debris. Each sensor 130 may be configured to generate a signal corresponding to the deflection of a respective movable pad 120. The sensors 130 may be load cells, strain gauges, pressure sensors, or any other selected sensors.

Figure 15:
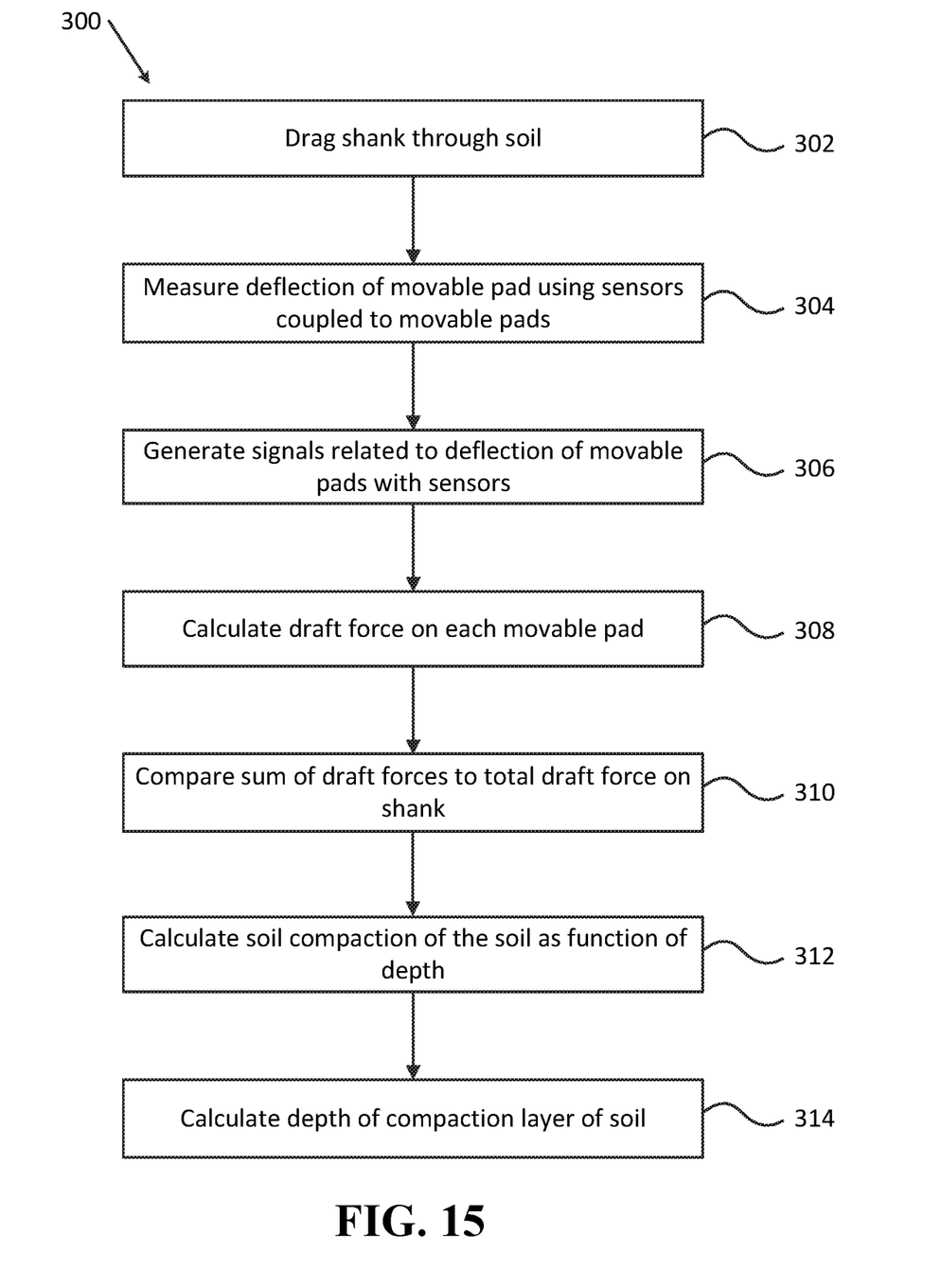
FIG. 15 is a simplified flow chart illustrating a method of measuring properties of soil.

FIG. 15 is a simplified flow chart illustrating a method 300 of measuring a property of soil. Block 302 represents dragging a shank through soil, such as the shank 110 shown and described above. Block 304 represents measuring deflection of movable pads relative to the shank as the shank is dragged through the soil using sensors coupled to the movable pads. In block 306, signals related to the deflection of the movable pads are generated with the sensors. In block 308, the draft force on each movable pad is calculated. Alternatively, a compressive force on each movable pad may be calculated. In block 310, the sum of the draft forces on each movable pad is compared to the total draft force on the shank. This may be used to calibrate the apparatus or verify proper operation of the apparatus. In block 312, soil compaction is calculated as a function of depth in the soil. In block 314, a depth of a compaction layer of the soil is calculated.

Additional non limiting example embodiments of the disclosure are described below.

Embodiment 1: An apparatus for measuring a soil condition, the apparatus comprising a shank configured to engage with a drawbar, an array of movable pads carried by the shank, and a plurality of sensors. Each of the movable pads are spaced at different distances from a point at which the shank is configured to engage the drawbar. Each sensor is coupled to at least one movable pad of the array of movable pads and configured to measure deflection of the at least one movable pad relative to the shank as the shank is dragged through soil by the drawbar.

Embodiment 2: The apparatus of Embodiment 1, wherein each sensor is configured to generate a signal corresponding to the measured deflection.

Embodiment 3: The apparatus of Embodiment 2, further comprising a receiver in communication with the sensors, the receiver configured to receive the signals from the sensors.

Embodiment 4: The apparatus of Embodiment 3, further comprising a processor configured to calculate a property of the soil.

Embodiment 5: The apparatus of Embodiment 4, further comprising a transmitter configured to transmit the property of the soil.

Embodiment 6: The apparatus of any one of Embodiment 1 through Embodiment 5, wherein the sensors comprise strain gauges.

Embodiment 7: The apparatus of any one of Embodiment 1 through Embodiment 6, wherein the movable pads are hingedly coupled to the shank.

Embodiment 8: The apparatus of any one of Embodiment 1 through Embodiment 6, wherein the movable pads are slidingly coupled to the shank.

Embodiment 9: The apparatus of any one of Embodiment 1 through Embodiment 8, wherein the movable pads of the array are disposed on or over a lateral surface of the shank.

Embodiment 10: The apparatus of Embodiment 9, further comprising a second array of movable pads on or over a second lateral surface of the shank opposite the first lateral surface, and a second plurality of sensors. Each sensor is coupled to at least one movable pad of the second array of movable pads and configured to measure deflection of the at least one movable pad relative to the shank as the shank is dragged through soil.

Embodiment 11: The apparatus of Embodiment 10, wherein each movable pad of the second array is offset from the movable pads of the array.

Embodiment 12: The apparatus of any of Embodiment 1 through Embodiment 8, wherein the movable pads of the array are arranged along a rear of the shank.

Embodiment 13: The apparatus of any of Embodiment 1 through Embodiment 12, further comprising a strain gauge configured to measure a total draft force of soil acting on the shank.

Embodiment 14: A method of measuring a property of soil, the method comprising dragging a shank through soil, the shank carrying an array of movable pads, and measuring deflection of the movable pads relative to the shank as the shank is dragged through soil using a plurality of sensors coupled to the movable pads. Each of the movable pads are spaced at different distances from a drawbar engaging the shank.

Embodiment 15: The method of Embodiment 14, further comprising generating signals with the sensors, the signals related to the deflection of the movable pads.

Embodiment 16: The method of Embodiment 14 or Embodiment 15, further comprising calculating soil compaction of the soil as a function of depth.

Embodiment 17: The method of Embodiment 16, further comprising calculating a depth of a compaction layer of the soil.

Embodiment 18: The method of any one of Embodiment 14 through Embodiment 17, further comprising calculating a draft force on each of the movable pads.

Embodiment 19: The method of Embodiment 18, further comprising comparing a sum of the draft forces on each of the movable pads to a total draft force on the shank.

All references cited herein are incorporated herein in their entireties. If there is a conflict between definitions herein and in an incorporated reference, the definition herein shall control.

While the present disclosure has been described herein with respect to certain illustrated embodiments, those of ordinary skill in the art will recognize and appreciate that it is not so limited. Rather, many additions, deletions, and modifications to the illustrated embodiments may be made without departing from the scope of the invention as hereinafter claimed, including legal equivalents thereof. In addition, features from one embodiment may be combined with features of another embodiment while still being encompassed within the scope of the invention as contemplated by the inventors. Further, embodiments of the disclosure have utility with different and various agricultural machine types and configurations.

What is claimed is:

1. An apparatus for measuring a soil condition, the apparatus comprising:
   a shank configured to engage with a drawbar;
   an array of movable pads disposed on or over a lateral surface of the shank, each of the movable pads spaced at different distances from a point at which the shank is configured to engage the drawbar; and
   a plurality of sensors, each sensor coupled to at least one movable pad of the array of movable pads and configured to measure deflection of the at least one movable pad relative to the shank as the shank is dragged through soil by the drawbar.

2. The apparatus of claim 1, wherein each sensor is configured to generate a signal corresponding to the measured deflection.

3. The apparatus of claim 2, further comprising a receiver in communication with the sensors, the receiver configured to receive the signals from the sensors.

4. The apparatus of claim 3, further comprising a processor configured to calculate a property of the soil.

5. The apparatus of claim 4, further comprising a transmitter configured to transmit the property of the soil.

6. The apparatus of claim 1, wherein the sensors comprise strain gauges.

7. The apparatus of claim 1, wherein the movable pads are hingedly coupled to the shank.

8. The apparatus of claim 1, wherein the movable pads are slidingly coupled to the shank.

9. The apparatus of claim 1, further comprising:
   a second array of movable pads on or over a second lateral surface of the shank opposite the first lateral surface; and
   a second plurality of sensors, each sensor coupled to at least one movable pad of the second array of movable pads and configured to measure deflection of the at least one movable pad relative to the shank as the shank is dragged through soil.

10. The apparatus of claim 9, wherein each movable pad of the second array is offset from the movable pads of the array.

11. The apparatus of claim 1, wherein the movable pads of the array are arranged along a rear of the shank.

12. The apparatus of claim 1, further comprising a strain gauge configured to measure a total draft force of soil acting on the shank.

13. A method of measuring a property of soil, the method comprising:
   dragging a shank through soil, the shank carrying an array of movable pads disposed on or over a lateral surface of the shank, each of the movable pads spaced at different distances from a drawbar engaging the shank; and
   measuring deflection of the movable pads relative to the shank as the shank is dragged through soil using a plurality of sensors coupled to the movable pads.

14. The method of claim 13, further comprising generating signals with the sensors, the signals related to the deflection of the movable pads.

15. The method of claim 13, further comprising calculating soil compaction of the soil as a function of depth.

16. The method of claim 15, further comprising calculating a depth of a compaction layer of the soil.

17. The method of claim 13, further comprising calculating a draft force on each of the movable pads.

18. The method of claim 17, further comprising comparing a sum of the draft forces on each of the movable pads to a total draft force on the shank.

* * * * *